(12) United States Patent
Varani et al.

(10) Patent No.: US 6,919,072 B2
(45) Date of Patent: *Jul. 19, 2005

(54) METHODS AND COMPOSITIONS FOR REDUCING COLLAGEN LOSS DUE TO CHRONOLOGICAL AGING IN HUMAN SKIN

(75) Inventors: James Varani, Ann Arbor, MI (US); Gary J. Fisher, Ann Arbor, MI (US); John J. Voorhees, Ann Arbor, MI (US); Sewon Kang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/458,355

(22) Filed: Jun. 10, 2003

(65) Prior Publication Data

US 2004/0034098 A1 Feb. 19, 2004

Related U.S. Application Data

(62) Division of application No. 09/028,435, filed on Feb. 24, 1998, now Pat. No. 6,630,516.
(60) Provisional application No. 60/040,594, filed on Feb. 25, 1997, provisional application No. 60/042,976, filed on Apr. 8, 1997, and provisional application No. 60/073,214, filed on Jan. 30, 1998.

(51) Int. Cl.[7] ............................. A61K 7/42; A61K 7/00; A61K 31/59; A61K 31/185; A61K 31/16; A61K 31/07

(52) U.S. Cl. ........................... 424/59; 424/60; 424/400; 424/401; 514/167; 514/576; 514/629; 514/725

(58) Field of Search ........................... 424/59, 60, 400, 424/401; 514/167, 576, 629, 725

(56) References Cited

U.S. PATENT DOCUMENTS 6,630,516 B2 * 10/2003 Varani et al. ................ 514/725

\* cited by examiner

Primary Examiner—Shelley A. Dodson
(74) Attorney, Agent, or Firm—Bradley N. Ruben

(57) ABSTRACT

Chronological aging of human skin can be delayed with the topical application of an MMP inhibitor, preferably a retinoid (an indirect MMP inhbitor); retinoids also normalize procollagen biosynthesis. Chronological aging, or natural aging, is evidenced in elderly (80+ years old) skin by increased MMP levels and decreased procollagen levels when compared with younger individuals. Prophylactic treatment of not yet chronologically-aged skin with a retinoid both inhibits degradation of dermal collagen and restores procollagen synthesis. Biopsied sections from elderly skin show that a single treatment of chronologically-aged skin with a retinoid can increase epidermal thickness, improve the dermal collagen density, and promote the formation of rete pegs and dermal papillae. Such benefits are helpful in preventing bruising, tearing, and ulceration of elderly skin. Accordingly, prophylactic treatment begun much earlier in life with an MMP inhibitor and/or a retinoid delays the onset of such symptoms.

18 Claims, 18 Drawing Sheets

FIGURES 3A-3B
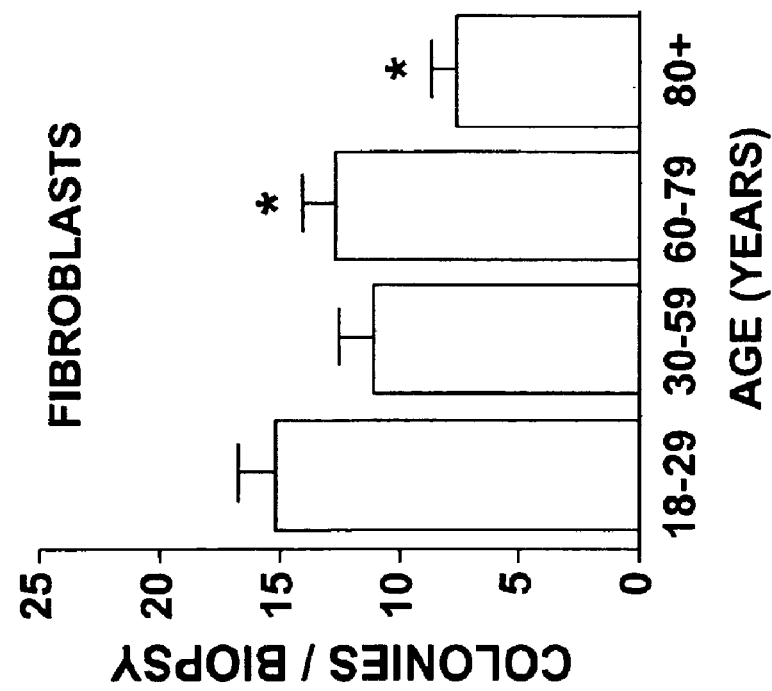
Figure 3A
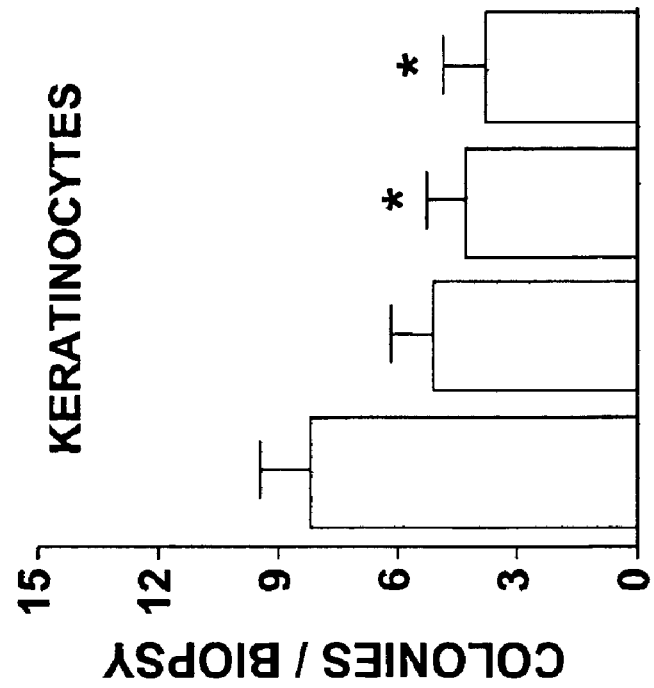
Figure 3B

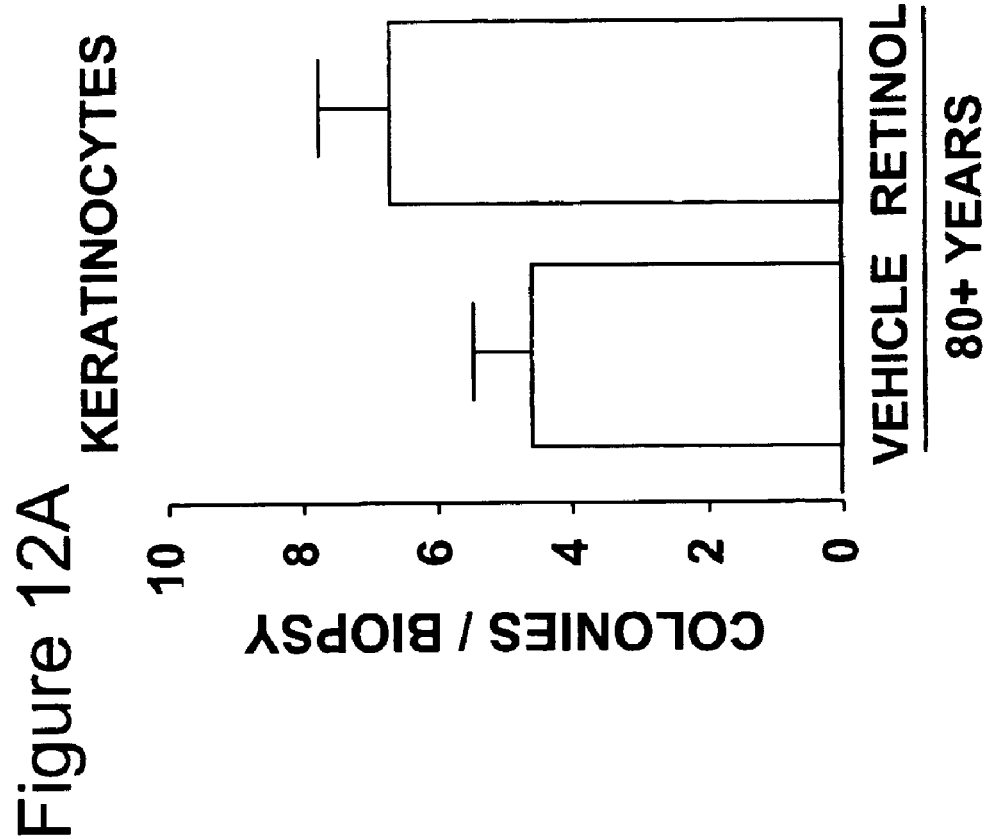
Figure 12A / Figure 12B

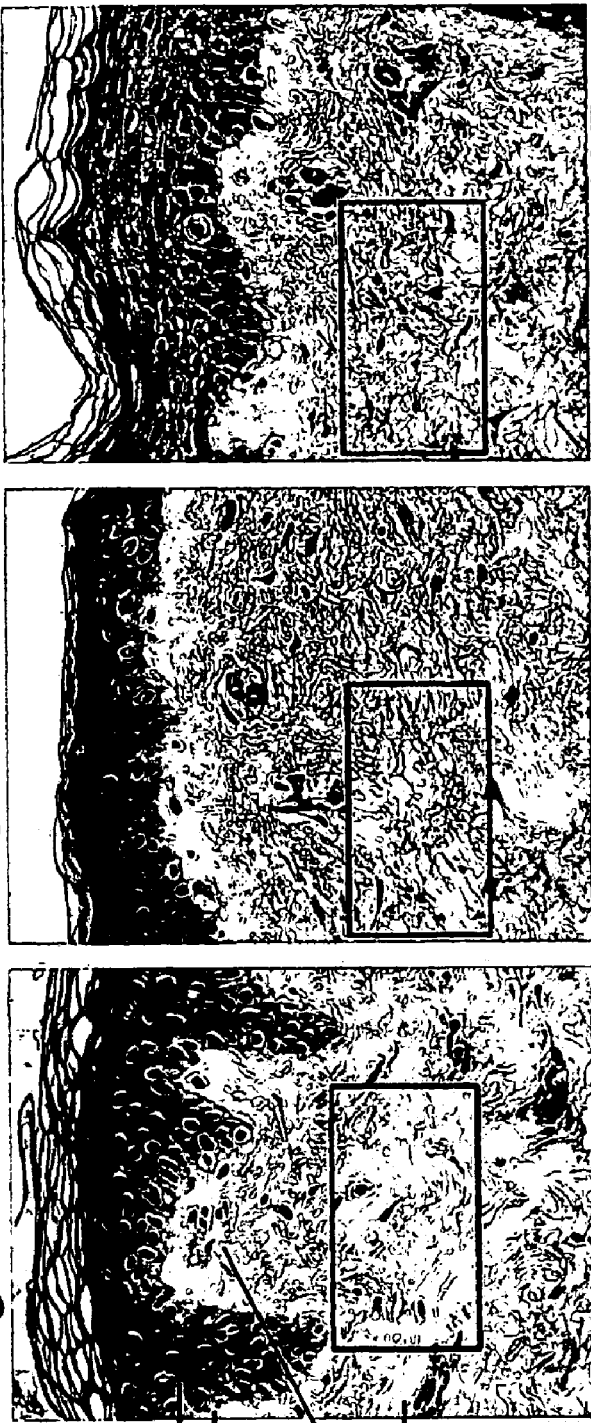

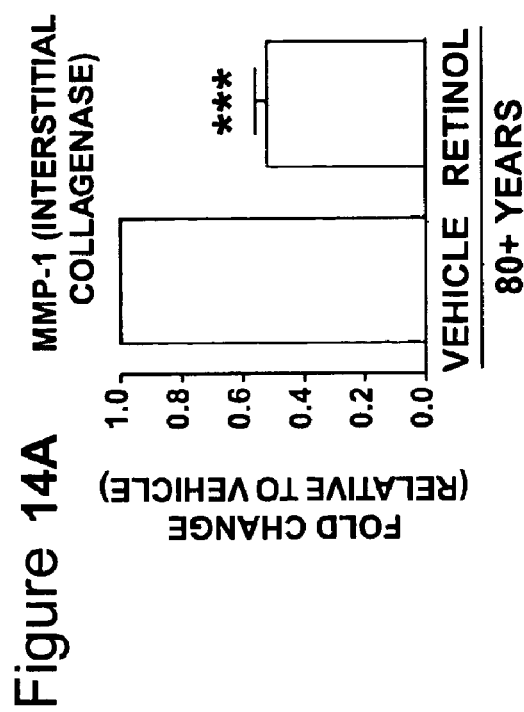
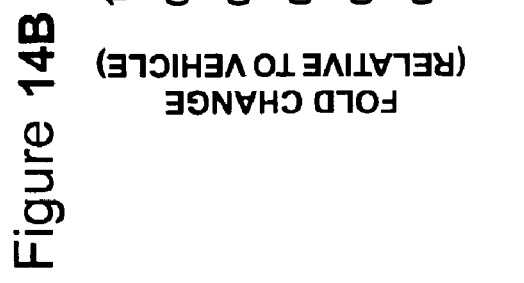
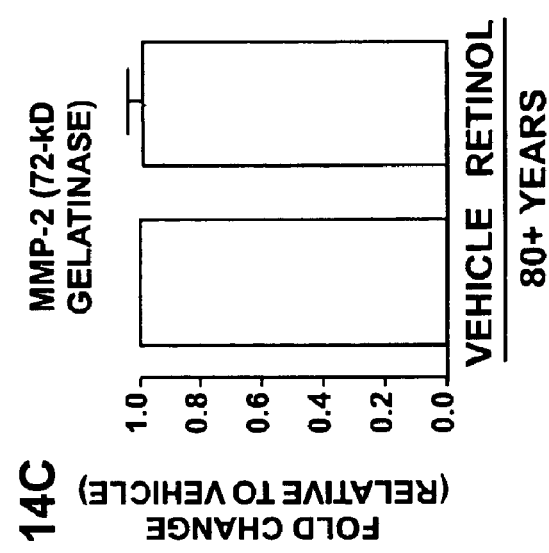
Figure 14A
Figure 14B
Figure 14C

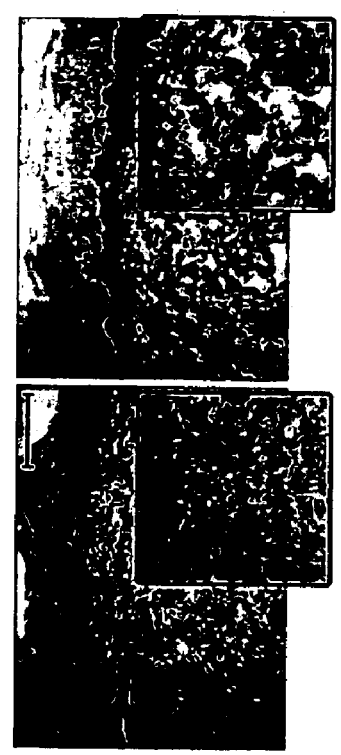
Figure 18C Type III Procollagen VEH ROL
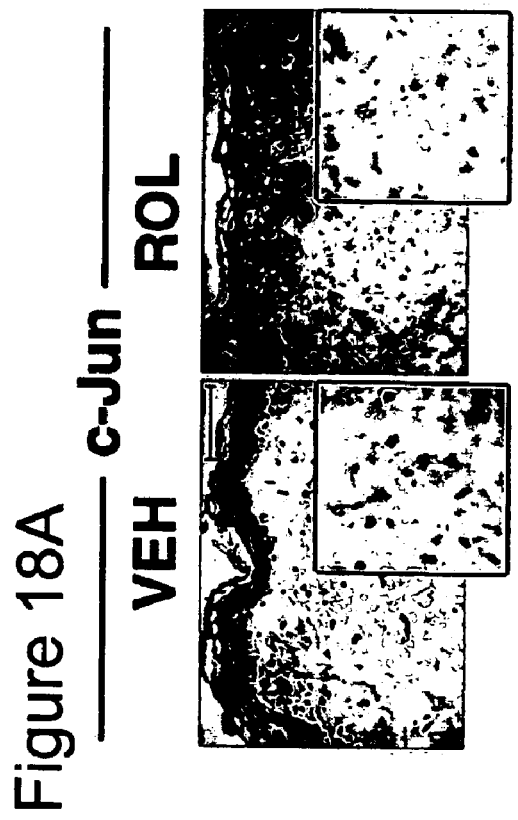
Figure 18A c-Jun VEH ROL
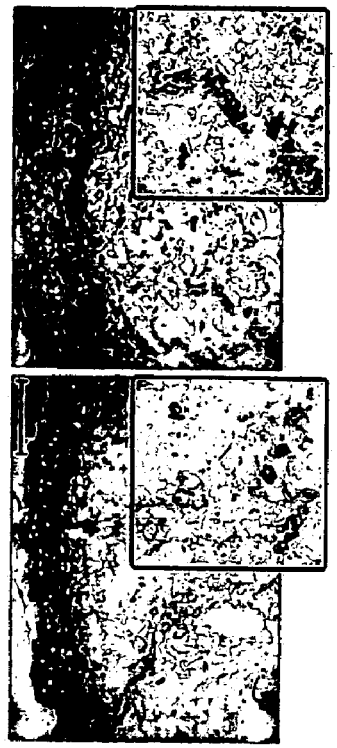
Figure 18B Type I Procollagen VEH ROL

METHODS AND COMPOSITIONS FOR REDUCING COLLAGEN LOSS DUE TO CHRONOLOGICAL AGING IN HUMAN SKIN

RELATED APPLICATIONS

This application is based on provisional applications 60/040,594, filed 25 Feb. 1997, 60/042,976, filed 8 Apr. 1997, and 60/073,214, filed 30 Jan. 1998, and is a divisional of utility application Ser. No. 09/028,435, filed 24 Feb. 1998, now U.S. Pat. No. 6,630,516, the disclosures of which are incorporated herein by reference.

BACKGROUND OF THE INVENTION

1. Field of the Invention

This invention relates to methods and compositions, especially those comprising retinoids, preferably topically applied to elderly skin, which are useful for improving keratinocyte and fibroblast proliferation, decreasing matrix metalloproteinase (MMP) expression, and improving collagen synthesis in elderly skin, thus providing as an effect the rejuvenation of aged skin.

2. The State of the Art

As far as mammals go, humans are essentially hairless; that is, most of the skin of the human body can be seen without interference from hair. The skin is thus exposed to whatever insults (natural and man-made) the environment harbors. Since it was first understood that the sun caused erythema, people have taken measures to avoid its "harmful rays." A century ago, in Elizabethan England, it was the fashion to avoid the sun at all costs. Yet the skin of those Elizabethians still wrinkled and displayed other signs of chronological aging.

Human skin is a complex organ which extends over the entire body. There are different types of skin at different portions of the body; for example, facial skin is different from that of the scalp, and even the skin on the front (palm) of the hand is different than that on the back of the hand. Although the type of skin can vary over a person's body, skin is generally composed of two main layers of tissue. The epidermis or cuticle, the outermost layer, is composed of three superficial and two deep layers. The derma, corium, or cutis vera, the true skin, is composed of a papillary layer above and a reticular layer below.

Since ancient times, a variety of substances have been applied to the skin to improve its appearance, generally by affecting the outermost layer of the skin, or to treat a skin ailment, generally by affecting the true skin. More recently, efforts have been made to rejuvenate the skin and reclaim the elasticity and suppleness lost from exposure to sunlight (UV radiation) and weather.

There is a difference between the physiology of chronologically-aged or intrinsically-aged skin (old skin) in comparison with that of photoaged skin. Old skin typically maintains a smooth and unblemished appearance, in comparison with the leathery, blotchy, and often deep wrinkling of photoaged skin. The epidermis of old skin is typically thinner than normal, whereas that of photoaged aged skin is typically thicker than normal (acanthotic) and atrophies over time. Photoaged skin typically has a large Grenz zone (a wide band of eosinophilic material just beneath the epidermis, and collagen formation and structures indicative of wound healing) which is absent from chronologically-aged skin. See also N. A. Fenske and C. W. Lober, "Structural and functional changes of normal aging skin," *J. Am. Acad. Dermatol.*, 15:571–585 (1986).

Kligman et al., in EP-A2-0 379,367 describe a method for the treatment or prevention of intrinsically aged skin with retinoids. Kligman et al. tested all trans-retinoic acid (as Retin-A® cream) on albino hairless mice and on 5 elderly Caucasian women; only clinical observations were made of the women before and after the study, and only one biopsy was reported taken and this occurred six months into the treatment (i.e., no reference biopsy was taken from this subject before treatment or from an early period of treatment).

U.S. Pat. Nos. 3,932,665 and 4,934,114 disclose the use of retinal (Vitamin A aldehyde), respectively, for the treatment of acne and for the treatment of skin keratoses; see also U.S. Pat. No. 3,060,229. Retinal and it derivatives have also been found as useful in the treatment of such conditions as wrinkles, warts, psoriasis, eczema, dandruff, and the like (see EP-A2-0 391 033). There are also a number of suggestions that tretinoin can heal or reverse the effects of photoaging. Albert M. Kligman, "Current Status of Topical Tretinoin in the Treatment of Photoaged Skin," *Drugs & Aging*, 2(1):7–13 (1992); and Chas. N. Ellis et al., "Tretinoin: Its Use in Repair of Photodamage," and A. S. Zelickson et al., "Topical Tretinoin in Photoaging: An Ultrastructural Study," both in *Journal of Cutaneous Aging & Cosmetic Dermatology*, Vol. 1, No. 1, p. 33–40 and 41–47 (1988).

Burger et al., in U.S. Pat. No. 5,665,367, describes compositions for topical application to the skin that contain naringenin and/or quercetin, and a retinoid. The compositions are described as useful for treating many unrelated skin conditions, such as wrinkles, acne, skin lightening, and age spots. The action of their composition on human skin is described with respect to an enzyme (transglutaminase) important to the formation of the cell envelope and thus to the epidermis. In contrast, the present invention is directed to changes in the dermis and the proliferation of beneficial dermal cells and structures.

SUMMARY OF THE INVENTION

The primary invention is the discovery of a method for rejuvenating human skin. As used with respect to the description and claiming of this invention, "rejuvenating" includes the steps of simultaneously preventing collagen degradation and stimulating the formation of new collagen in aged human skin. The invention is based on biopsies of treated and untreated sun-protected human skin from aged (80+) volunteers as compared with biopsies of sun-protected skin from younger individuals. In comparison with the skin from younger people, aged skin is thinner, has fewer keratinocytes and fibroblasts, has less dense and more disorganized connective tissue, has higher activity levels of cJUN kinase and matrix metalloproteinases, and has reduced levels of cyclin $D_2$ and procollagen synthesis; while total levels of ERK growth factor are the same in both young and old skin, the activated (phosphorylated) form of ERK is diminished in older skin.

In summary, we have found as one invention that aged human skin can be rejuvenated by the topical administration of one or more compounds in amounts effective to inhibit collagen degradation and to promote procollagen synthesis, the application preferably being performed on a regular basis. A preferred class of compounds that perform both functions are retinoids, especially retinol and retinoic acid.

Aged human skin can be benefitted by enhancing procollagen synthesis. We have found as another invention that procollagen levels can be normalized in aged human skin by the preferably regular application to the skin of effective amounts of a retinoid.

In addition to treating and/or prevent chronological aging of the skin, our discovery that effective amounts of a retinoid applied to the skin can normalize procollagen synthesis provides another invention in the prevention (prophylaxis) of skin ulcers. By increasing the collagen content of the skin, the form, strength, and function of the skin is enhanced. Increased procollagen synthesis, and thus an increase in collagen content of the skin, mitigates the loss of strength and support that the degraded collagen would have to provide for the epidermis, and so improved procollagen synthesis is expected to diminish the occurrence and/or severity of skin ulcers.

In connection with the foregoing, we have found as yet other inventions that keratinocytes and fibroblasts, each beneficial to the integrity of the skin, are each increased in number by the topical application of a retinoid, again applied preferably on a regular basis. Fibroblasts are trophic to the epidermis; under normal conditions they secrete a number of growth factors (e.g., FGF, IGF, and KGF, among others) and produce procollagen that enters the dermal matrix and become structural collagen.

An additional invention is preventing chronological aging of human skin by applying to the skin, preferably on a regular basis, a retinoid in amounts effective to normalize procollagen synthesis; in preferred embodiments, the treatment also include inhibition of collagen degradationby the use of an MMP inhibitor.

In additional embodiments, prophylaxis and treatment of dermal chronoaging are each enhanced by applying along with the active ingredient at least one additional compound selected from: a sunscreen for at least one of $UVA_1$, $UVA_2$, and UVB; an antioxidant; an MMP (matrix metalloproteinase) inhibitor; and mixtures thereof.

BRIEF DESCRIPTION OF THE FIGURES

FIG. 3 depicts the differences in in vivo keratinocyte density (3A) and fibroblast density (3B) among the age populations we studied.

FIGS. 12A and 12B show the change in keratinocyte density (12A) and fibroblast density (12B) after retinol treatment based on in vivo observations in the oldest population we studied.

FIGS. 13A through 13F shows stained cross-sections and closeups from the skin of a young individual (13A and 13B), and elderly individual (13C and 13D), and the same elderly individual after a single application of 0.1% retinol (occluded, left for seven days) (13E and 13F).

FIGS. 14A, 14B, and 14C show the change in collagenase (14A) and gelatinase (14B and 14C in the skin of the oldest population we studied after treatment with retinol.

FIGS. 18A, 18B, and 18C are stained cross-sections from the skin of an elderly individual after treatment with retinol showing the change in c-JUN (18A), type I procollagen (18B), and type III procollagen (18C).

DESCRIPTION OF PREFERRED EMBODIMENTS OF THE INVENTION

Figure 1:
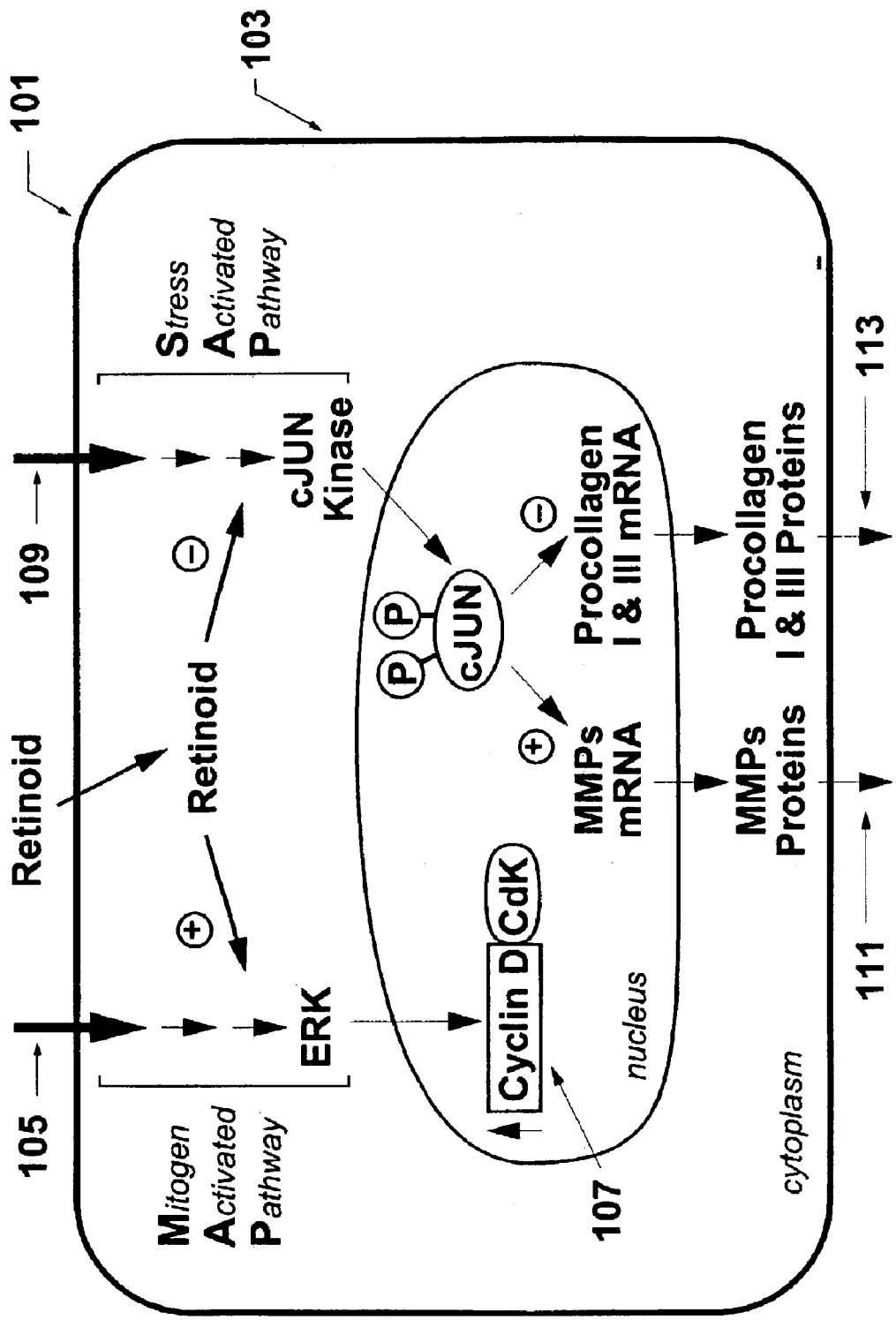
FIG. 1 depicts our representation of certain MAP and SAP pathways in an idealized skin cell.

FIG. 1 depicts certain degradative pathways that effect the functioning of an idealized skin cell based on our findings. The particularly important causes of chronological aging of human skin likely vary among a population of elderly humans, including such factors as diet, sun exposure, and other environmental factors. In general, though, we believe that chronological skin aging is due to activation of the mitogen-activated pathways (MAPs) and the stress-activated pathways (SAPs). Surprisingly, this is contrary to conventional wisdom; in comparison with our inventions relating to photoaging of human skin, we have found that both chronoaging and photoaging of human skin have a similar molecular pathophysiology. MAPs activate growth factors necessary for healthy skin; as the epidermis grows its cells eventually become the dermis, and so interference with the MAPs can lead to thinning and chronologically-aged skin because of the reduced number of cells entering the dermis. Almost conversely, SAPs activate factors that arrest growth or degrade the dermal matrix, induce apoptosis and collagenases, and thereby lead to aging. Chronological aging of skin might be expected to include some interference with the MAPs and/or some activation of the SAPs: we have found that both events occur in chronologically-aged human skin. As shown in FIG. 1, the idealized skin cell 101 has a cell membrane 103 across which various compounds pass or at which they interact with the cell via receptors at the cell's surface. One group of inputs indicated by 105 activates the MAP pathway, which induces a cascade resulting in the formation of ERK, a growth factor; once activated (by phosphorylation), ERK induces Cyclin D formation 107 in the cell nucleus, with the result that growth of the cell is promoted. The other group of inputs is indicated by 109, which activates the SAP pathway and, while activated by external inputs, is also based on inputs from intercellular signalling. The SAP pathway leads to increases in cJUN kinase activity; once activated (again by phosphorylation), cJUN becomes a cofactor for AP-1, which leads to MMP formation 111 and export from the cell, and the resulting degradation of collagen in the dermal matrix. Matrix metalloproteinases (MMPs) include collagenases, gelatinases, and other enzymes naturally occuring in human skin that degrade collagen.

We have found that there is an age-associated decrease in keratinocytes and fibroblasts as determined from comparisons of replicate 4-mm punch biopsies obtained from the sun-protected skin of 40 individuals, ranging from 18 to over 80 years of age. Keratinocytes are the principal cell at the epithelial continuum in the rete mucosa below the epidermis; the cells of the epidermis arise by differentiation of basal keratinocytes, some of which differentiate through successive overlying layers to become the stratum corneum. The biopsies evidenced mean decreases of 27% (keratinocytes) and 39% (fibroblasts) when the youngest age group (18–29 years old) was compared with the oldest age group (80+ years old) ($p<0.1$ for both cell types). These findings are further confirmed by our discovery of age-associated decreases in the ex vivo growth of keratinocytes (54% decrease) and fibroblasts (50% decrease) compared between the same two age groups ($p<0.1$ for both cell types).

We have found that there is also an age-associated increase in connective tissue disorganization and/or degeneration (2.25-fold increase in oldest group compared with youngest group; $p<0.05$). The disorganization and degeneration of the connective tissues were measured by microscopic histological examination of biopsied skin tissue obtained from these elderly subjects and compared with the histology of skin biopsied from young individuals. We have now also discovered an age-related increase in MMP-1, MMP-2, and MMP-9 when these groups of young and old individuals are compared (respectively, mean increases of 40%, 82%, and 53%, and respectively $p<0.01$, $p<0.001$, and $p<0.01$). These results were determined using replicate 4-mm punch biopsies from our 40 volunteer subjects.

To investigate the treatment of chronologically-aged skin, an additional 17 subjects having an age of at least 80 years old were treated for 7 days with 1% retinol under occlusion or with vehicle alone. The vehicle was composed of a mixture of ethanol and polyethylene glycol in a 70:30 volumetric ratio. In comparing vehicle-treated skin with untreated skin from individuals of the same elderly age range, there were no statistically significant differences in any of the aforementioned parameters. However, in comparing retinol-treated skin with vehicle-treated skin from the same individuals, there were increased numbers of keratinocytes and fibroblasts per section in the retinol-treated skin (273% ($p<0.001$) and 30% ($p<0.05$) mean increases, respectively) as well as increased ex vivo keratinocyte and fibroblast growth (46% and 215%, respectively, with $p<0.05$ for both). Additionally, there was decreased expression of MMP-1 and MMP-9 (48% and 39% decreases, respectively, with $p<0.001$ for both enzymes), but no significant change in the expression of MMP-2.

Figure 7:
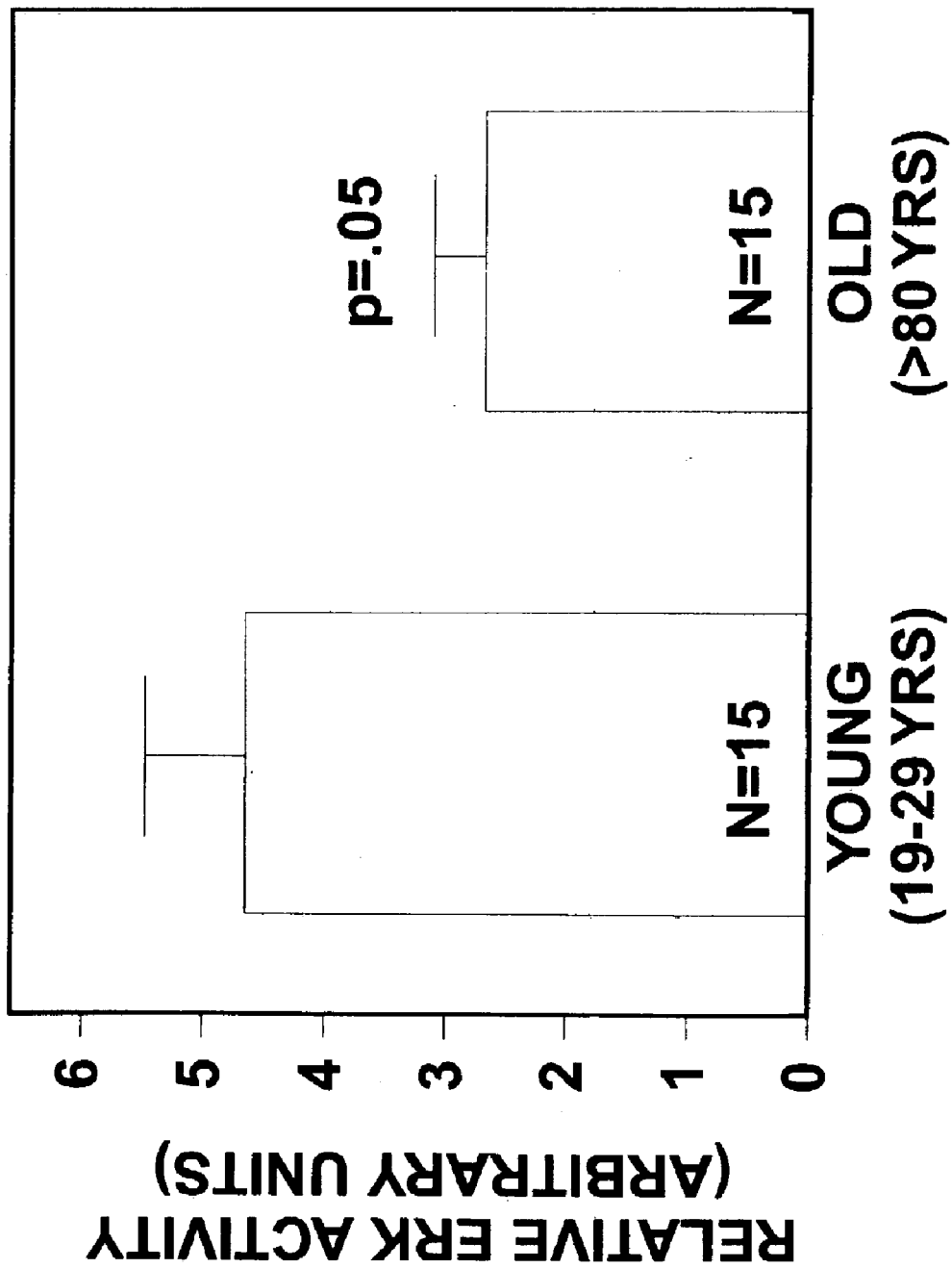
FIG. 7 depicts the ERK activity expression between the youngest and oldest age populations we studied.

In studying chronological skin aging, it would be helpful to determine an approximate "steady state" value for various factors in the MAPs naturally occuring in skin (the skin biopsied was typically unexposed to the sun and other environmental factors, and was usually taken from the buttocks or hip). FIG. 7 shows our finding for the steady state activity of ERK skin biopsies from volunteers, both old (over 80+ years old) and young (19–29 years old), generally according to methods as described herein. The histograph in FIG. 7 shows that the relative activity of ERK (e.g., based on phosphorylated ERK) in the skin of elderly volunteers is almost half of its activity in the skin of younger people.

Figure 8:
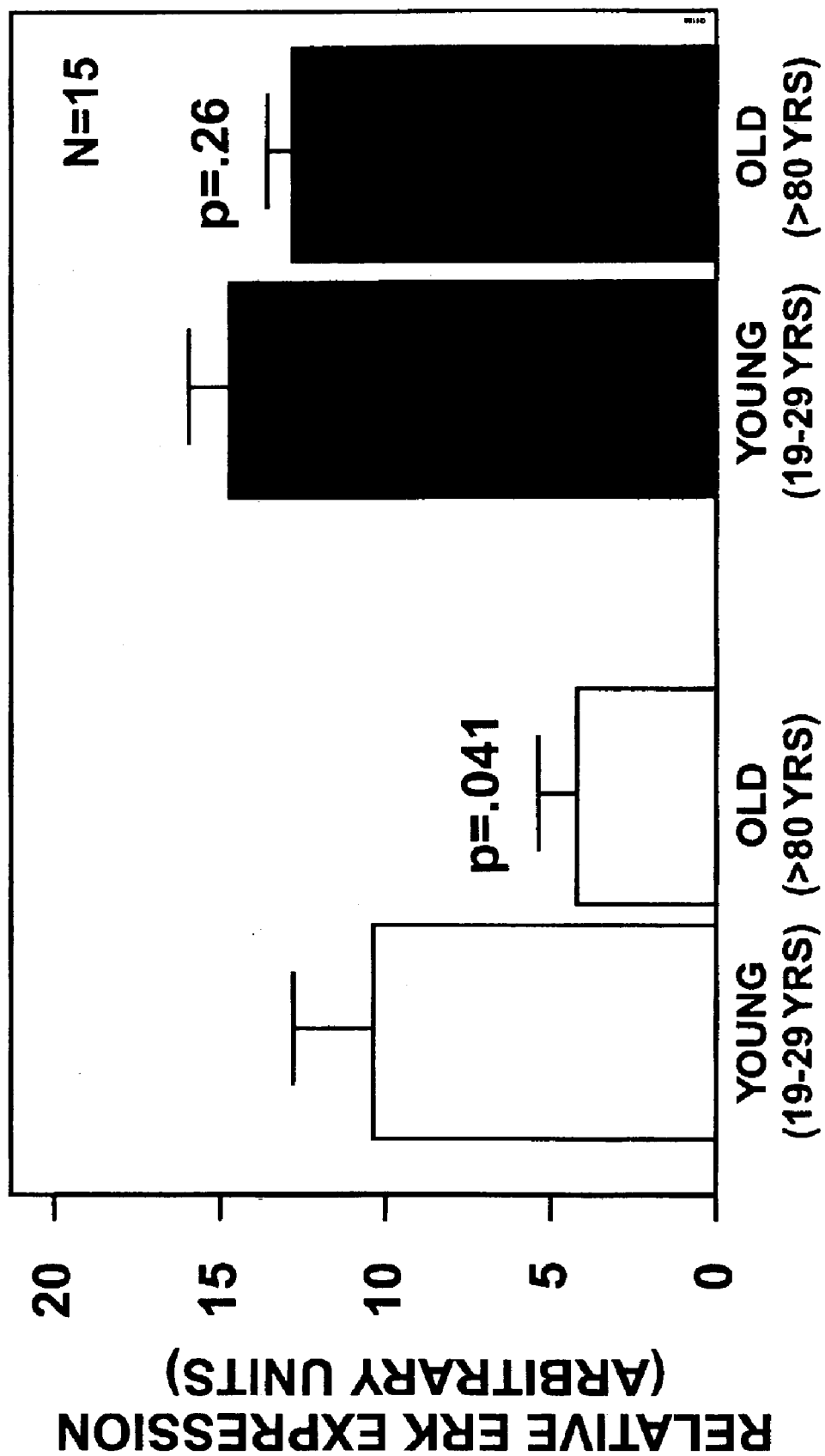
FIG. 8 depicts the amount (solid) and phosphoration degree (open) of ERK between the youngest and oldest age populations we studied.

Shown in FIG. 8 is the presence of phosphorylated myelin basic protein ("MBP"), used as an artificial substrate for ERK phosphorylation, for these same young and old subjects. (That is, if activated ERK is present, MBP will be phosphorylated.) In elderly subjects the ERK growth factor present in the biopsied skin is barely active.

Reduced growth factor activity might be expected to result in the aged appearance of skin, so we tested fifteen volunteers to determine the relative amounts of ERK in the skin in its phosphorylated (activated) and inactive forms; when activated, ERK stimulates cell growth. As shown in FIG. 8, elderly subjects had essentially the same amount of total ERK in their skin as subjects half a century younger (solid bars), but had significantly less of the active, phosphorylated form of ERK (open bars). Accordingly, we have found that the reduced activity of ERK in elderly skin is not due to a reduction in the total amount of ERK, but rather in the low concentration of the activitated form.

Figure 9:
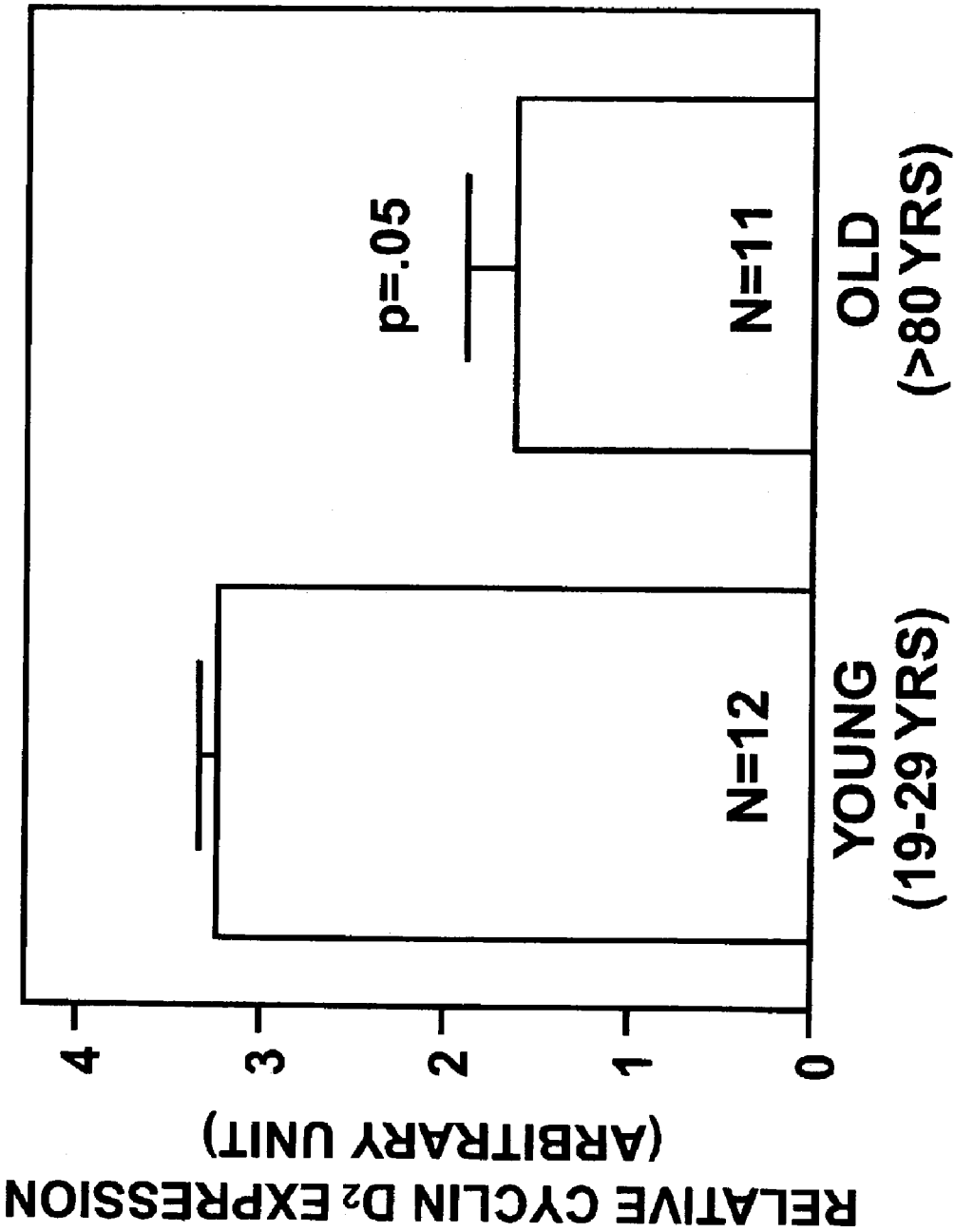
FIG. 9 depicts the cyclin $D_2$ expression between the youngest and oldest age populations we studied.

Finally in the MAP pathway shown in FIG. 1, ERK induces Cyclin $D_2$, which is required for cell growth. Again, interference with this MAP signalling agents would lead to reduced production of Cyclin $D_2$, leading to retarded cell growth and repair, and so the effects of aging on the skin would be promoted. FIG. 9 depicts our results analyzing twelve young subjects and eleven elderly subjects for expression of Cyclin $D_2$ in normally covered (sun-protected) skin. The histograph of FIG. 9 shows that chronologically-aged skin has a significant reduction in the amount of Cyclin $D_2$ expressed. Both the amount and the activity of the Cyclin $D_2$ is decreased in elderly skin.

These results on tests of various signalling components of MAPs important for fostering growth in human skin indicate that chronological aging in human skin is promoted by a breakdown or lessening of the components of that pathway that promote cell growth. As skin ages, various breakdowns in the MAPs can lead to reduced cell growth that results, ultimately, in aged skin. Our in vivo test results of normally unexposed skin show a breakdown in the MAP that is likely to result in aged skin.

Returning again to FIG. 1, activation of SAP (stress-activated pathways 109) promotes the degradation of skin through the production of MMPs including collagenases. The SAP can be activated or up-regulated by UV radiation (as described in our copending application now issued as U.S. Pat. No. 5,837,224, and provisional applications 60/048,520, filed Jun. 4, 1997, and 60/057,976, filed Sep. 5, 1997, all related to photoaging of human skin, the disclosures of which are incorporated herein by reference), tumor necrosis factors (e.g., TNF-$\alpha$), interlukins (e.g., IL-1$\alpha$), and other stresses. As described in the just noted '771 application and '520 and '976 provisional applications, AP-1 induces MMPs, enzymes that degrade collagen. As shown in FIG. 1, the formation of AP-1 is driven by the heterodimenzation of cJUN protein with cFOS protein in the skin.

Figure 5:
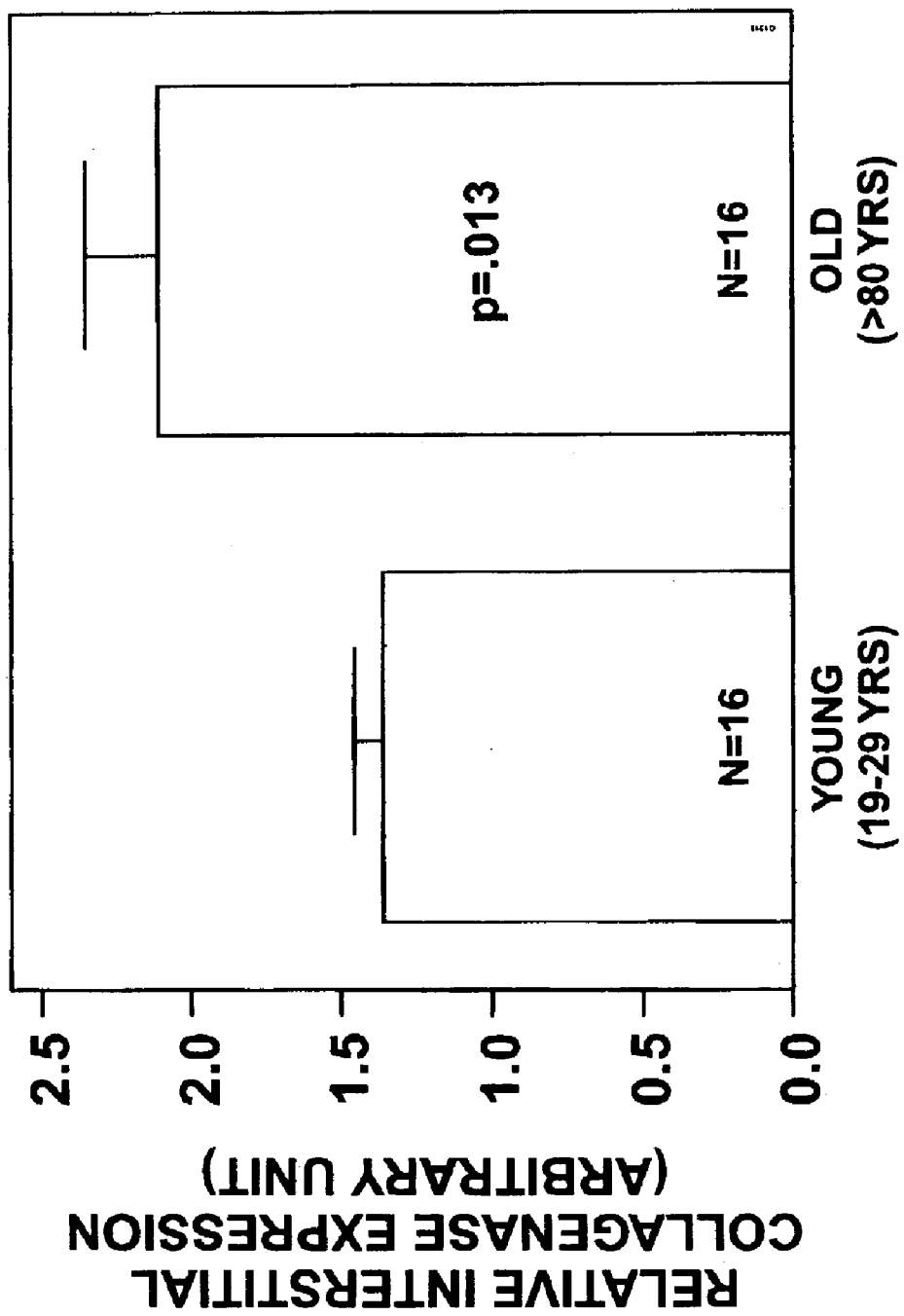
FIG. 5 depicts the interstitial collagenase expression between the oldest and the youngest of the age populations we studied.
Figure 10:
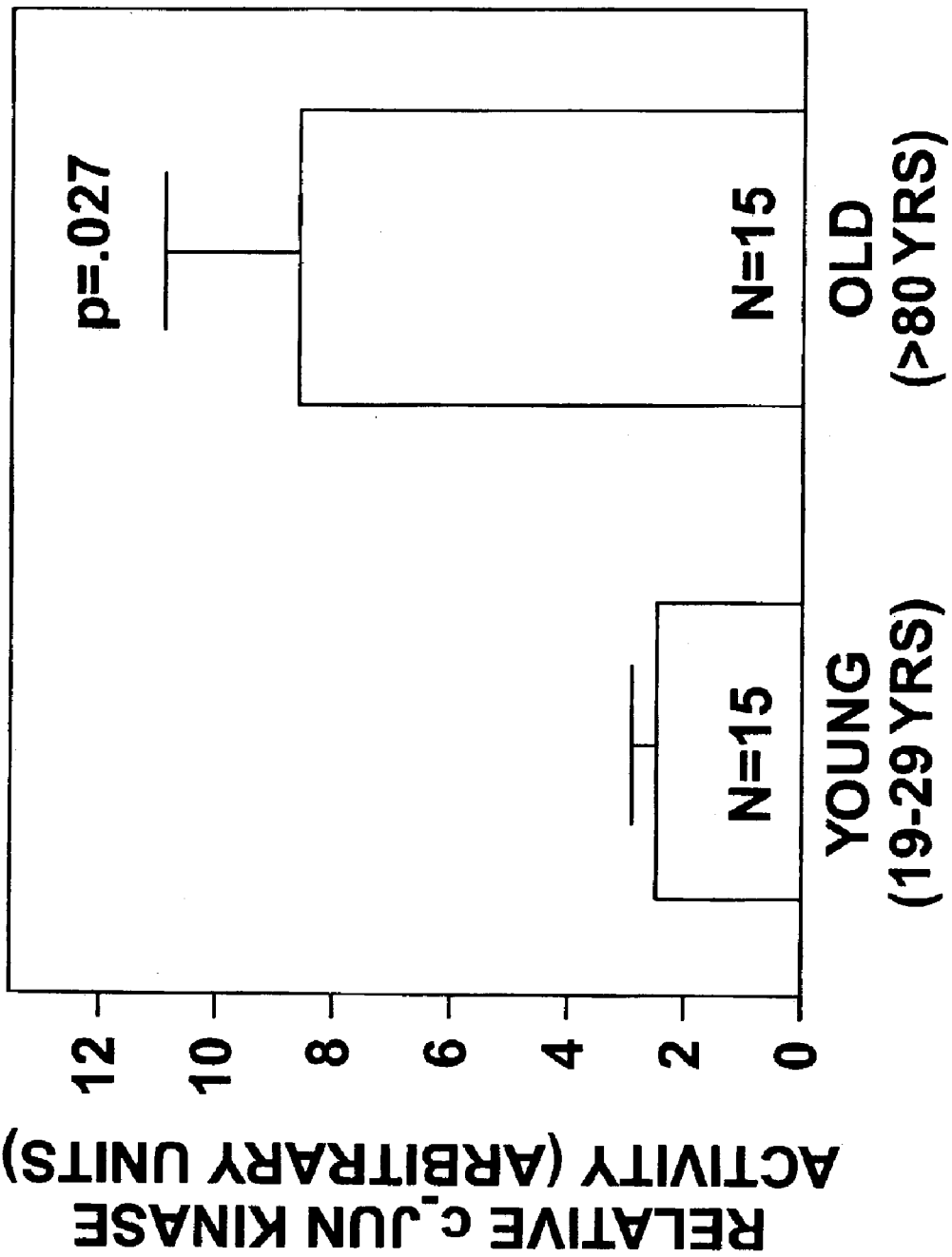
FIG. 10 depicts the cJUN kinase activity between the youngest and oldest age populations we studied.

We tested fifteen subjects in two age groups, young subjects (19–29 years old) and elderly subjects (over 80 years old) to determine the degree of activation of the SAP in each group. FIG. 10 shows that in vivo samples of unexposed skin from the young subjects had about 25% of the relative cJUN kinase activity than did unexposed skin from elderly subjects. In the elderly subjects, that unexposed skin has a significant amount of cJUN activity. From these results, one would then expect correspondingly elevated levels of AP-1 and MMPs in the skin of elderly. As shown in FIG. 5, interstitial collagenase activity measured from the skin of 16 individuals in each of the two groups was found to be present in elderly skin in amounts nearly double those found in younger subjects.

Figure 6:
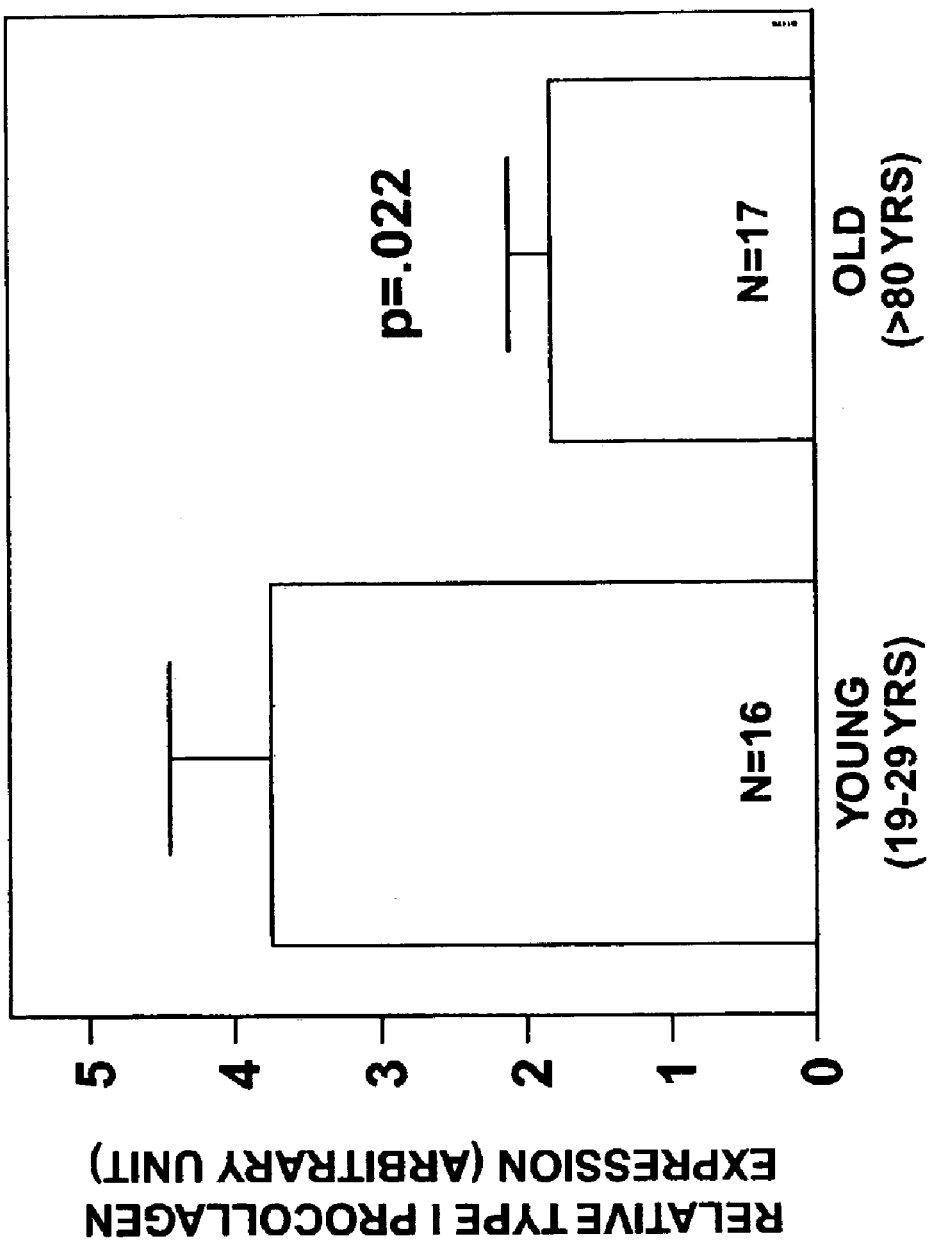
FIG. 6 depicts the type I procollagen expression between the youngest and oldest age populations we studied.

Returning again to FIG. 1, it can be seen that activation of SAPs results in multiple assaults on collagen in the skin, by degradation through MMPs induced by AP-1 in turn induced by cJUN. FIG. 6 depicts the analysis of the presence of Type I procollagen in in viva samples of unexposed skin taken from each of the two groups of individuals tested (yound and old). We have found that about twice as much Type I procollagen is expressed in unexposed (sun-protected) young skin than in unexposed elderly skin. While not desirous of being constrained to a particular theory, we believe that these results show that increased cJUN kinase activity interferes with the synthesis of procollagen (soluble collagen) which is then exported (113, with reference to FIG. 1) from the cell into the matrix to become structural collagen (insoluble collagen); we believe that activated cJUN inhibits one or more steps in the synthesis of procollagen, as shown by the hash mark. Further, then, while we have shown in the above-referenced photoaging patent applications that we can interfere with UV-induced production of collagenases, there are additional pathways involved with chronological aging, and so pathways specific to chronoaging of the skin are not necessarily effected when a patient is treated for photoaging of the skin.

Taken together, the control pathways shown in FIG. 1 indicate that chronological aging of skin can be caused by deactivation of the MAPs and/or by activation of the SAPs. In fact, we have found that both events occur in elderly skin. The results depicted in FIGS. 7–9 show that the sun-protected skin of elderly persons (which skin has generally not been exposed to the sun on a chronic basis) has reduced amounts of active ERK and a reduced amount of Cyclin $D_2$, which lead to a reduction in cell growth. In addition (as shown above in FIG. 6), there is also a reduction in the amount of procollagen synthesized. If there is less cell growth in the dermis, then the epidermal covering is also likely to be compromised. On the other side (degradation of the dermis as opposed to creation of new dermis), the results depicted in FIGS. 4, 5, and 10 show that the unexposed skin of elderly persons has increased expression of cJUN protein and MMPs. The up-regulation of the degradative MMP enzymes and the down-regulation of procollagen synthesis result in a degradation of collagen, causing skin aging, and a decrease in the amount of new collagen formed, inhibiting repair of aged skin.

In view of the foregoing results, our invention is generally directed to the topical administration, preferably on a regular basis, of an amount of a retinoid, preferably retinol or retinoic acid, to the skin of an elderly person in amounts effective to induce the proliferation of at least one of keratinocytes and fibroblasts, to reduce the expression of MMPs, and/or to stimulate the synthesis of procollagen in the elderly person's skin back to normal levels.

This invention is also directed to inhibiting intrinsic aging of the skin (i.e., preventing or decreasing the rate and/or severity of chronoaging) by applying to the skin of an elderly person, preferably on a regular basis, an amount of an agent effective to inhibit at least one MMP. As we have found, chronologically aged human skin is characterized by a higher than normal concentration of MMPs. An agent effective to inhibit at least one MMP is selected from those that inhibit (a) the activity of an MMP, (b) the transcription of MMP, and (c) compatible mixtures thereof, especially where the MMP is active in the skin. Various inhibitors of MMPs are described in copending U.S. patent application Ser. No. 08/588,771, filed Jan. 19, 1996, and provisional applications 60/048,520, filed Jun. 4, 1997, and 60/057,976, filed Sep. 5, 1997, the disclosures of which are incorporated herein by reference.

Retinoids are one class of MMP inhibitors. The inhibitors of MMPs can act directly on the MMPs and/or on the transcription factors AP-1 and NF-kB by which MMPs are produced naturally. Aspirin and E5510 (described by Fujimori, T., et at., Jpn J Pharmacol (1991) 55(I):81–91) inhibit NF-kB activation. Retinoids such as those disclosed in U.S. Pat. No. 4,877,805 and the dissociating retinoids that are specific for AP-1 antagonism (such as those described by Fanjul, et al. in Nature (1994) 372:104–110), glucocorticoids, and Vitamin $D_3$ target AP-1. Compounds for enhancing the therapeutic effect of Vitamin $D_3$ are described in copending application Ser. No. 08/832,865 (J. Voorhees et al., "Method for Assessing 1,25(OH)$_2$D$_3$ Activity in Skin and for Enhancing the Therapeutic Use of 1,25(OH)$_2$D$_3$"), filed Apr. 4, 1997, the disclosure of which is incorporated herein by reference. Other retinoids, besides retinol, include natural and synthetic analogs of vitamin A (retinol), vitamin A aldehyde (retinal), vitamin A acid (retinoic acid (RA)), including all-trans, 9-cis, and 13-cis retinoic acid), etretinate, and others as described in EP-A2-0 379367, U.S. Pat. No. 4,887,805, and U.S. Pat. No. 4,888,342 (the disclosures of which are all incorporated herein by reference). Various synthetic retinoids and compounds having retinoid activity are expected to be useful in this invention, to the extent that they exhibit retinoid activity in vivo, and such are described in various patents assigned on their face to Allergan Inc., such as in the following U.S. Pat. Nos. 5,514,825; 5,698,700; 5,696,162; 5,688,957; 5,677,451; 5,677,323; 5,677,320; 5,675,033; 5,675,624; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos. 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like, the disclosures of all of the foregoing and following patents and literature references hereby incorporated herein by reference.

MMPs are also inhibited by BB2284 (described by Gearing, A. J. H. et al., Nature (1994) 370:555–557), GI129471 (described by McGeehan G. M., et al., Nature (1994) 370:558–561), and TIMPs (tissue inhibitors of metalloproteinases, which inhibit vertebrate collagenases and other metalloproteases, including gelatinase and stromelysin). Still other compounds useful for the present invention include hydroxamate and hydroxy-urea derivatives, such as Galardin, Batimastat, and Marimastat, and those disclosed in EP-A1-0 558635 and EP-A1-0 558648 (as useful for inhibiting MMPs in the treatment of, among other etiologies, skin ulcers, skin cancer, and epidermolysis bullosa). Retinoids have been reported by Goldsmith, L. A. (*Physiology, Biochemistry, and Molecular Biology of the Skin*, 2nd. Ed. (New York: Oxford Univ. Press, 1991), Chpt. 17) to cause an increase in steady state levels of TIMP mRNA that would suggest transcriptional control; although, based on our discoveries, we have found this is not true in human skin in vivo. Still other inhibitors of MMPs that can be applied topically and are useful in practicing the claimed invention include the tetracyclines and derivatives thereof, such as minocycline, roliteracycline, chlortetracycline, methacycline, oxytetracycline, doxycycline, demeclocycline, and the various salts thereof.

Because of possible allergic or sensitization reactions, the topical administration of tetracyclines should be monitored carefully for such untoward reactions. Other MMP inhibitors include genistein and quercetin (as described in U.S. Pat. No. 5,637,703, U.S. Pat. No. 5,665,367, and FR-A-2,671, 724, the disclosures of which are incorporated herein by reference) and related compounds, as well as other antioxidants such as NAC (N-acetyl cystein), green tea extract, and others.

The effective amount of the active ingredient applied to the skin is preferably in the range of about 0.001–5 wt. %, more preferably about 0.01–2 wt. %, still more preferably 0.1–1 wt. %, such as 0.4±0.25 wt. %, and most preferably 0.4±0.1% by weight of the composition. Compositions are formulated to provide preferably about 5 $\mu g/cm^2$ skin when applied. For example, a preferred composition for use in this invention is Retin-A® retinoic acid gel and cream (available from Ortho Pharmaceuticals) for the treatment of acne vulgaris, in strengths of from 0.01% to 0.1%; the vehicle preferably includes, depending upon the particular formulation, at least one of butylated hydroxytoluene, alcohol (denatured with t-butyl alcohol and brucine sulfate), stearic acid, isopropyl myristate, polyoxyl 40 stearate, stearyl alcohol, and the like, and compatible mixtures thereof.

FIGS. 12A and 12B demonstrate the effects of a 7-day in vivo retinol treatment on ex vivo growth of keratinocytes and fibroblasts extracted from biopsies of sun-protected skin take from individuals over age 80. FIGS. 12A and 12B show an age-associated decrease in ex vivo growth potential for both cell types. However, treatment with retinol for seven days substantially increased the growth of both cell types. In particular, keratinocytes increased about 30% while fibroblasts increased about 200%. Accordingly, the topical application of a retinoid to aged, sun-protected skin would be expected to increase the number of keratinocytes and/or the number of fibroblasts in the skin.

Figures 2A, 2B, 2C, 2D:
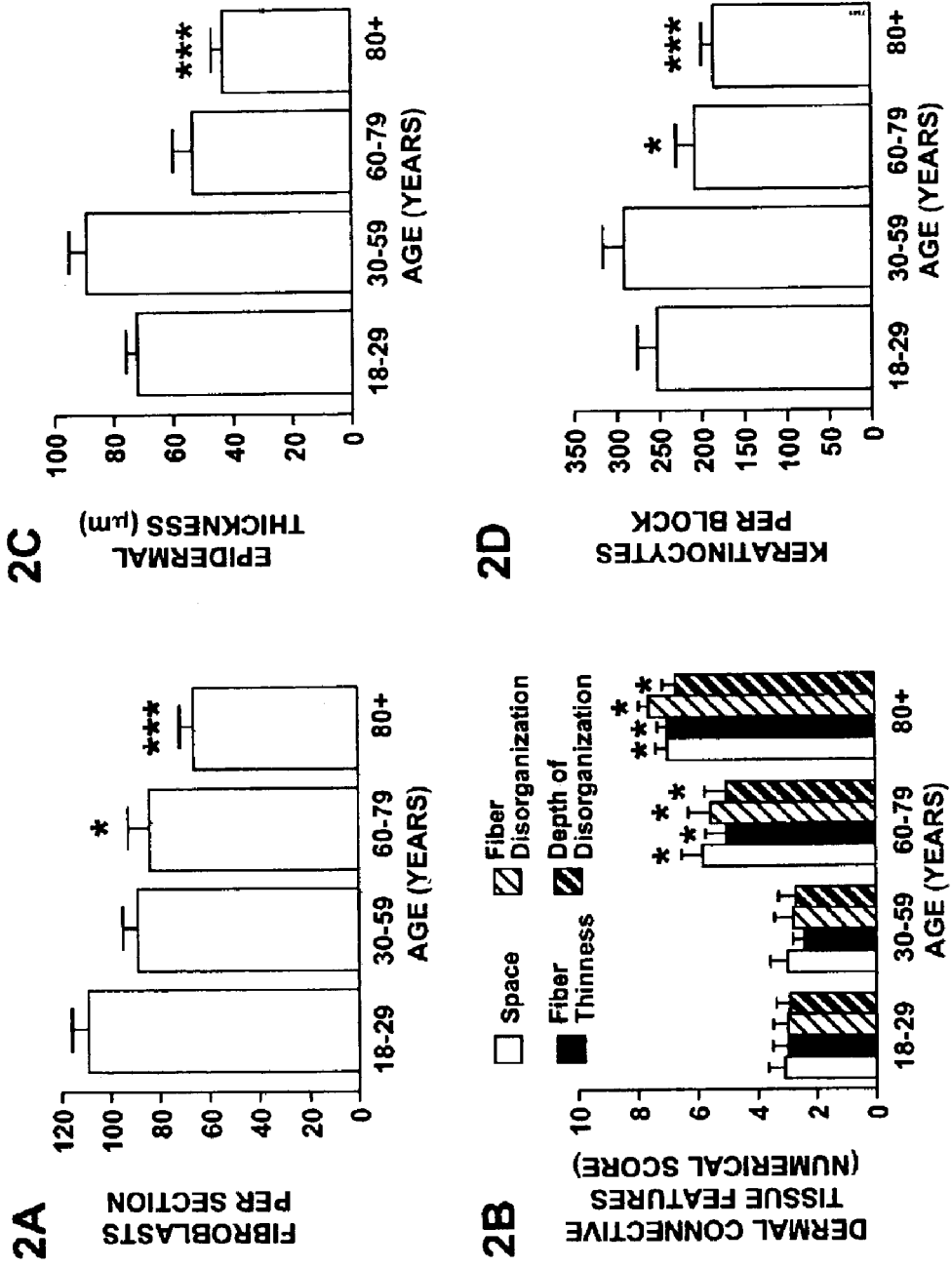
FIGS. 2A, 2B, 2C, and 2D depict the fibroblast density (2A), dermal connective tissue features (2B), epidermal thickness (2C), and keratinocyte density (2D) in all of the age populations we studied via biopsy.
Figure 11A:
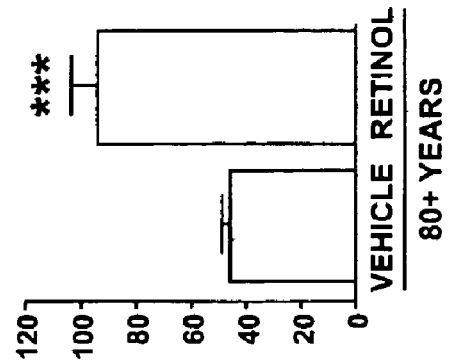
FIGS. 11A, 11B, 11C, and 11D depict the change in fibroblast density (2A), dermal connective tissue features (2B), epidermal thickness (2C), and keratinocyte density (2D) in the oldest population we studied after topical treatment with retinol.
Figure 11B:
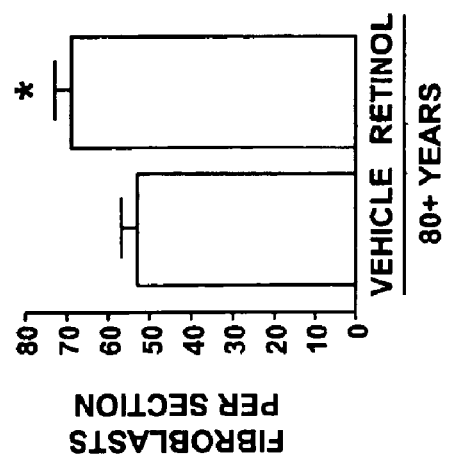
Figure 11C:
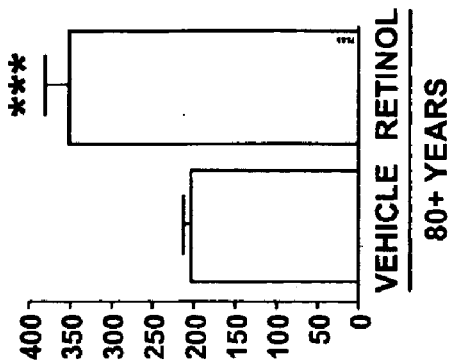
Figure 11D:
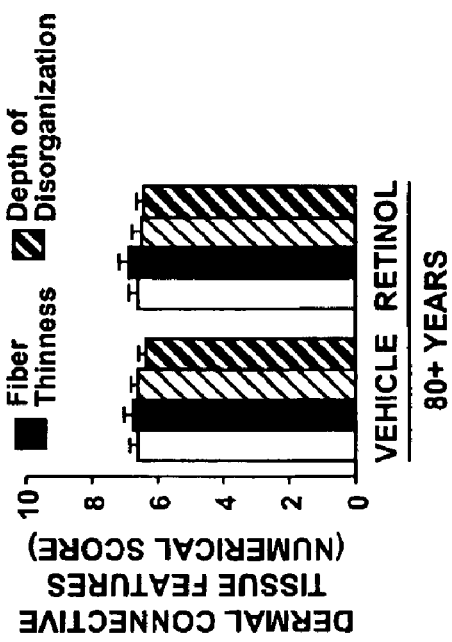

FIGS. 2A, 2B, 2C, and 2D represent morphometric data based on the entire population study we conducted. Age-associated changes in the skin are seen as a decrease in epidermal thickness above age 60 (FIG. 2C), a decrease in keratinocytes above age 60 (FIGS. 2D and 3A), a decrease in fibroblasts above age 30 and another above age 80 (FIGS. 2A and 3B), and an increase in the number of dermal connective tissue features above age 60 (FIG. 2B ). When comparisons are made between vehicle-treated skin and retinol (ROL) treated skin (that is, sun-protected skin treated once with 0.1% retinol, covered with a patch, left undisturbed for seven days, and then biopsied), the beneficial effects on the skin can be seen: treatment with retinol clearly improved the epidermal thickness (FIG. 11C)and the numbers of keratinocytes (FIGS. 11D and 12A) and fibroblasts (FIGS. 11A and 12B), although not much of a change in the number of dermal connective tissue features (FIG. 11B was apparent.

Figure 4A:
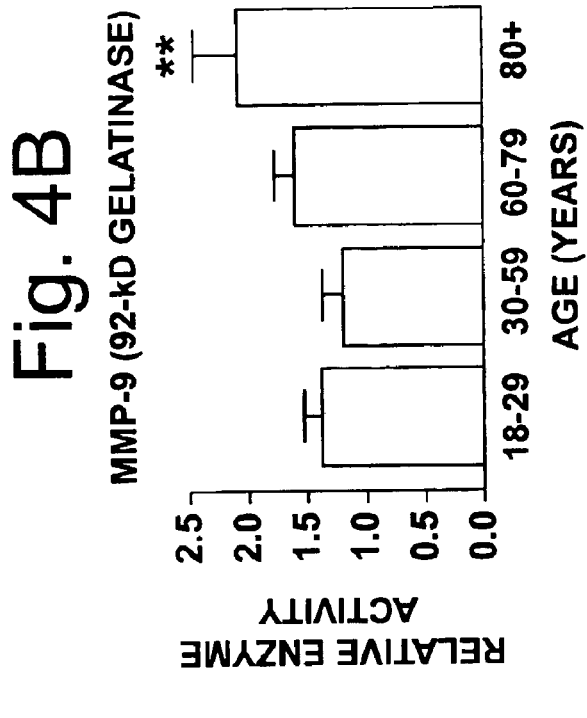
FIG. 4 depicts the differences in collagenase and gelatinase activity among the age populations we studied.
Figure 4B:
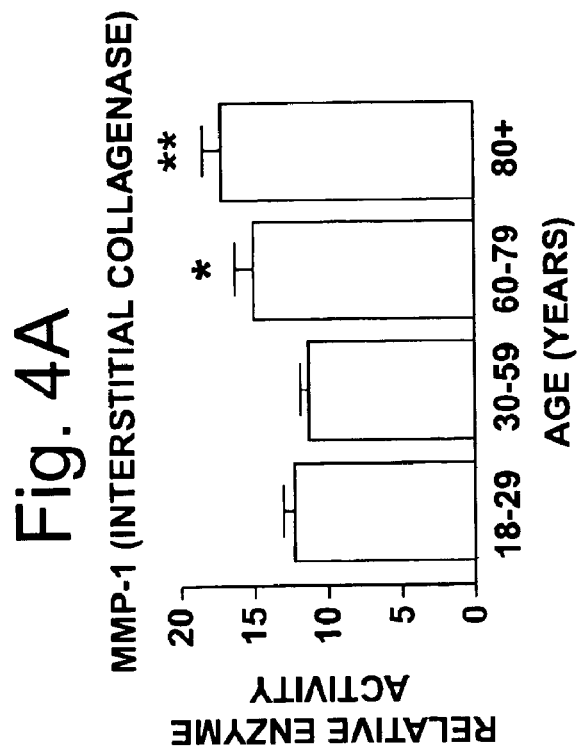
Figure 4C:
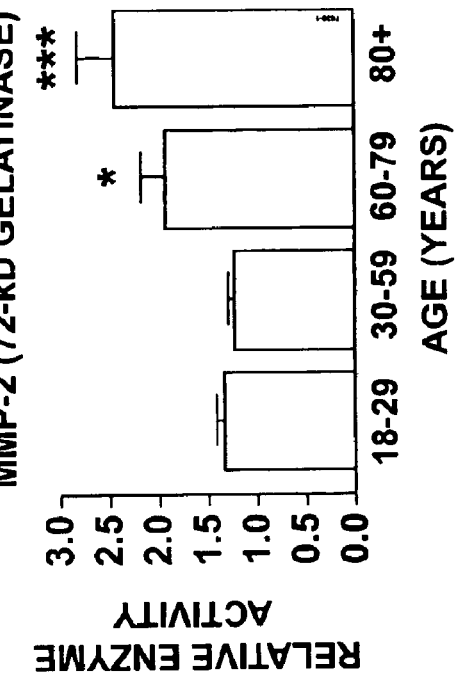

FIGS. 4A, 4B, and 4C depict the average MMP levels (for collagenase MMP-1 and gelatinases MMP-9 and MMP-2, respectively) as a function of age for sun-protected skin determined from biopsies taken from sun-protected skin of our volunteer population. It is seen from this data that the levels of all three of these MMPs are elevated in the skin of individuals of at least age 60, and even more elevated in those at least 80 years old. Treatment of elderly individuals with retinol significantly reduced the levels of MMPs 1 and 9 (FIGS. 14A and 14B as compared with a control treatment of the vehicle only, but did not appear to change the level of MMP-2 (FIG. 14C) present in sun-protected, chronically aged skin. (In FIGS. 4A, 4B, 4C, and 9A, 9B, and 9C the number of subjects for each figure was 10; "*" indicates $p<0.5$ versus the 18–29 year old values, "" indicates $p<0.1$, and "*" indicates $p<0.001$.)

Accordingly, in one embodiment the invention comprises a method of rejuvenating aged skin by the application of an effective, non-toxic amount of a retinoid for an effective period of time. The effective period of time is generally daily, preferably with only one application/administration of the composition each day. Preferred treatment and maintenance regimes use an effective amount of about 0.4% retinoid, although higher doses can be used where warranted. Retinol is the preferred retinoid.

In another embodiment, the invention provides a method of inducing in vivo keratinocyte and/or fibroblast proliferation by the topical administration of an effective, non-toxic amount of a retinol for an effective period of time. Again, treatment is preferably daily, once or twice, with the amount of retinoid preferably being 0.4%±0.25%.

In yet another embodiment, the invention reduces and/or inhibits MMP-1 and/or MMP-9 expression in elderly skin, by the topical administration of an effective amount of a retinol for an effective period of time. Again, treatment is preferably daily, once or twice, with the amount of retinoid preferably being 0.4%±0.25%.

As noted above, the decrease in keratinocytes and fibroblasts, and the increase in MMP expression, can be viewed as an age-related condition without resort to insults such as sun damage. This invention thus provides a prophylaxis against a detrimental change in any of these age-related parameters, as well as providing a treatment to ameliorate these detrimental etiological changes induced by aging.

In another aspect, this invention is directed to improving, or stimulating, the synthesis of procollagen in an elderly person's skin. We have found there is a significant reduction in procollagen synthesis in sun-protected skin of many (at least 50% of) aged individuals. Procollagen is a protein synthesized within skin cells and then secreted into the extracellular medium, where it is converted by naturally occurring enzymes into collagen. This reduced procollagen synthesis in an elderly person's skin is manifest as a reduced presence of procollagen protein in both the upper dermis (extracellular) and in fibroblasts throughout the dermis, and can be determined (e.g.) by immunohistochemistry.

It has been found unexpectedly that topical treatment of elderly, chronoaged skin with a retinoid results in a restitution of intracellular procollagen protein levels similar to those observed in young individuals (such as those aged 40 and younger). In particular, we have found that a single application of 0.1% retinol to chronologically-aged skin, covered with an air-permeable adhesive bandage, and examined seven days later, resulted in procollagen protein levels comparable to those found in sun-protected skin of significantly younger individuals (e.g., under age 40). It would be more preferable for elderly persons to apply the retinoid once or twice daily to maintain a therapeutic regimen, although the agent could be applied on a less frequent but preferably regular basis (e.g., every other day, or once weekly). It may also be desirable for the skin to be occluded from environmental insults, particularly sources of UV light, detergents and other harsh chemicals, and the like. Accordingly, it would be beneficial to add to the retinoid composition a UV sunscreen, an antioxidant, and the like.

The stimulation of procollagen production is an important factor in maintaining the integrity of chronologically-aged skin. Aged skin is thin and fragile due, in part, to reduced collagen content and reduced collagen fiber organization. Stimulation of procollagen synthesis by retinoids, and its subsequent conversion to collagen, would be expected to reduce the fragility, increase the thickness, and improve the appearance of aged skin. Accordingly, this invention provides methods for increasing procollagen concentrations, both intra- and extracellularly, and so also to improving collagen concentrations, all in chronologically-aged skin. Additionally, as shown herein, MMP levels are increased in elderly skin from those found in the skin of younger persons. Improved production of procollagen would be frustrated if the resulting collagen were degraded in the skin, and so treatment of elderly skin with both a retinoid and an MMP inhibitor is important for achieving the desired benefits of improved procollagen biosynthesis. In fact, we have found in skin not having a reduced level of collagen, treatment a retinoid does not elevate the collagen levels above normal; hence, our invention shows that application of a retinoid can restore collagen levels to their desired baseline value. Thus, our inventive treatment with a retinoid both increases the fibroblasts' production of (pro)collagen and interferes with the MAP activity that causes epidermal thinning.

Although retinol is the preferred compound for topical administration, effective derivatives of retinol that would be expected to be useful for practicing this invention include retinal, retinoic acid (including all trans, 9-cis, and 13-cis isomers) and derivatives thereof (such as 7,8-didehydroretinoic acid), and others as described by Kligman et al., referred to above, the disclosure of which is incorporated herein by reference, including cosmetically acceptable salts, esters, reverse esters, and ethers thereof, conjugates thereof, and mixtures thereof.

Figure 15:
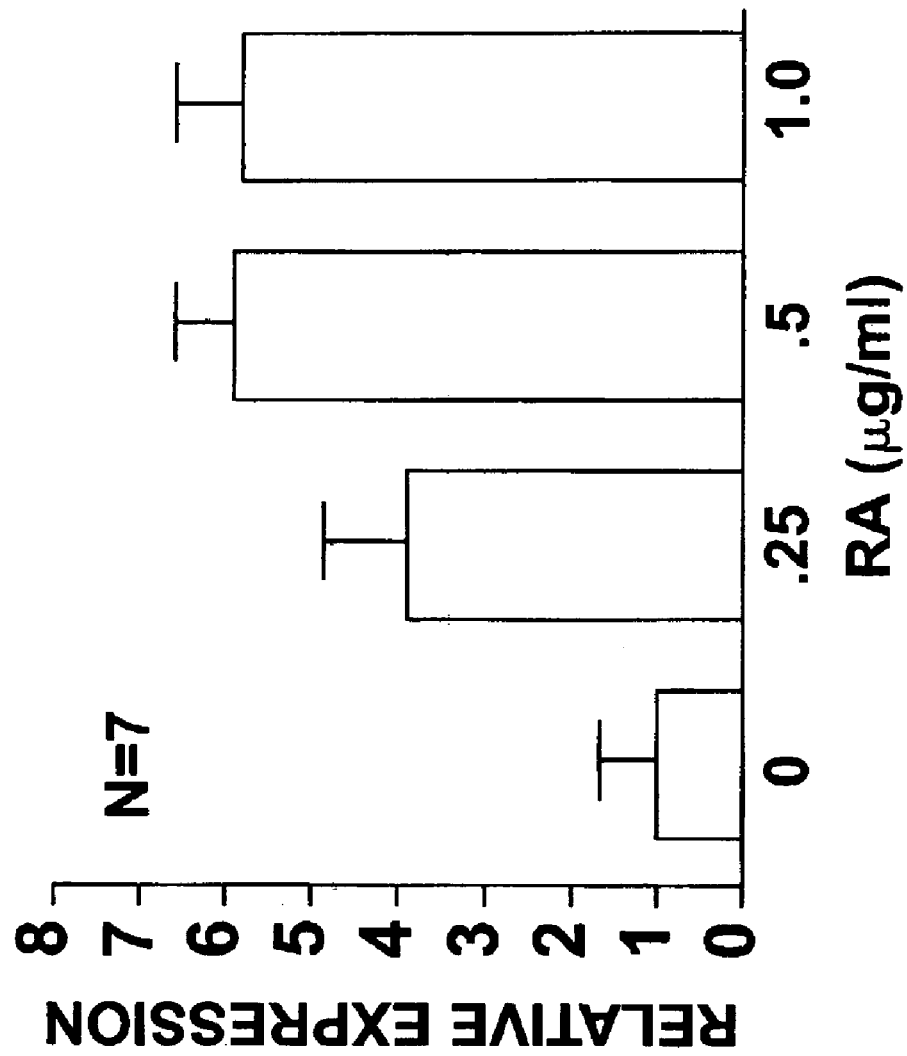
FIG. 15 depicts the response for the synthesis of type I collagen in ex vivo fibroblasts from elderly volunteers as a function of the retinoic acid dose concentration.
Figure 16:
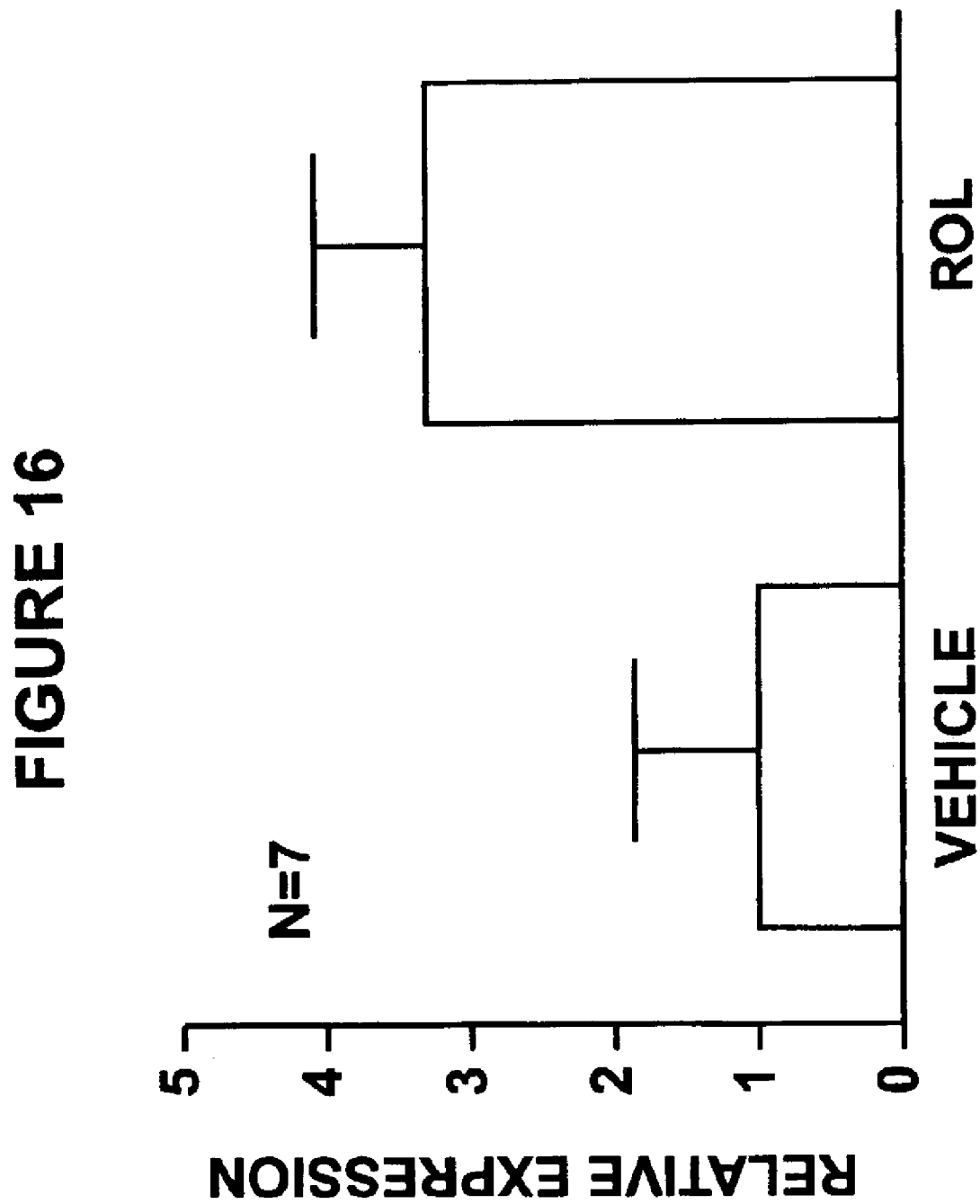
FIG. 16 depicts the response of procollagen α1(III) mRNA expression in human skin of the oldest population we studied after treatment with retinol.
Figure 17:
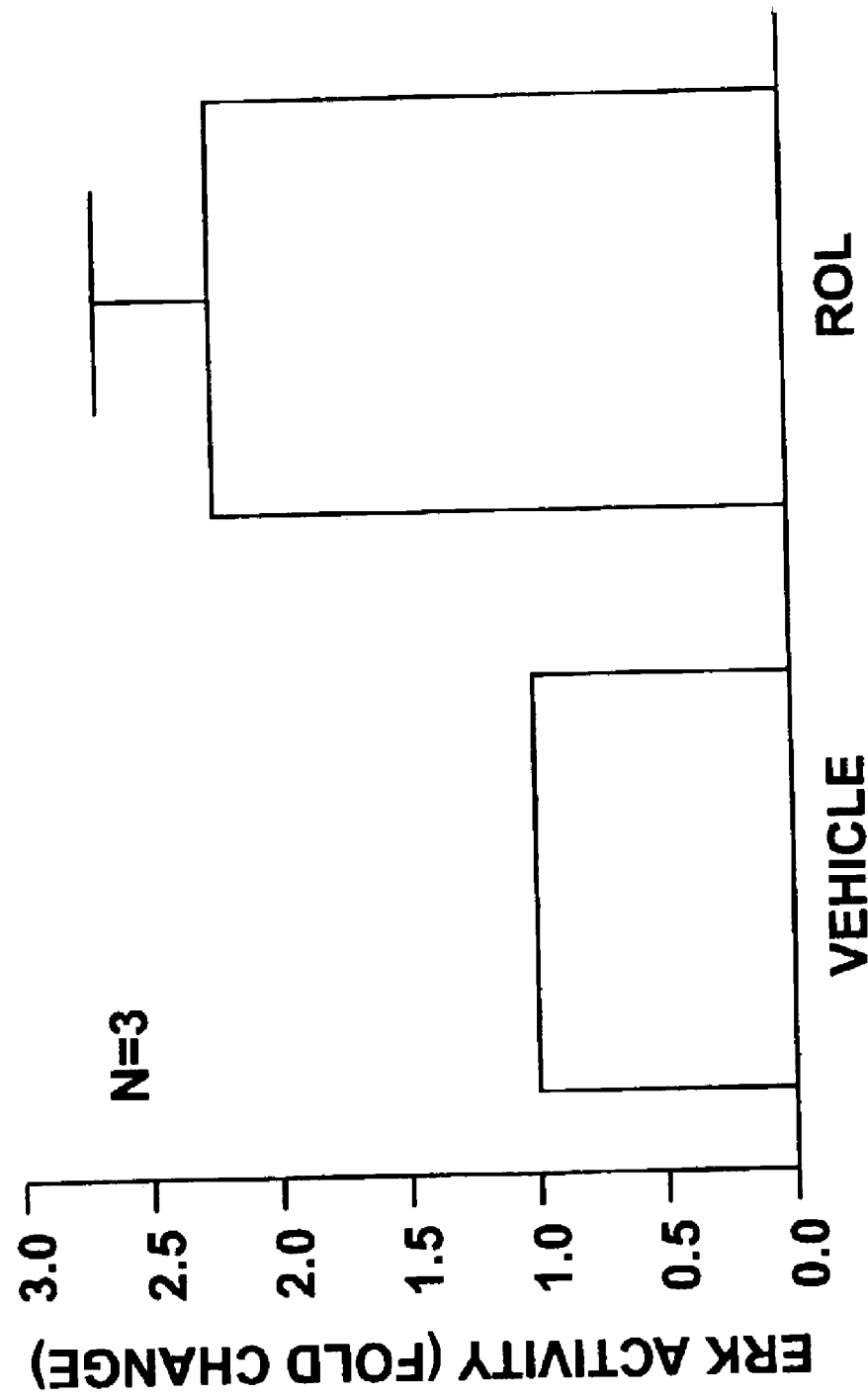
FIG. 17 depicts the response of ERK activity in human skin of the oldest population we studied after treatment with retinol.

Using the foregoing and analogous techniques, we have found that retinoic acid induces biosynthesis of collagen I in human dermal fibroblasts at concentrations of at least 0.5 $\mu$g/ml, and even as low as 0.25 $\mu$g/ml (FIG. 15) and that a retinol concentration of about $10^{-8}$ molar is sufficient for promoting procollagen expression in fibroblasts as determined by analyzing for mRNA expression (FIG. 16). Using a sample of seven volunteers over 80 years old and cultured fibroblasts from biopsy samples of their unexposd (sun-protected) skin, we confirmed these in vitro results by showing that a retinoic acid concentration of 0.25 $\mu$g/ml increases the relative expression of collagen three fold from that of untreated cells, and 0.5 and 1.0 $\mu$g/ml generally increased the biosynthesis of collagen in these cultured cells five-fold from untreated cells. These seven 80+ year old individuals were treated clinically with 1% retinol cream, applied once to sun-protected skin, covered with a patch, and left undisturbed for seven days. Biopsies of these treated area under the patch revealed that procollagen $\alpha 1(III)$ mRNA had increased in these individuals' skin about 2.5 times from that of control (vehicle-treated) areas treated by the same method (single application and covered for seven days) as shown in FIG. 16. FIG. 17 shows similar results increasing ERK activity after retinol treatment.

An increase in the pathway activity that causes an increased rate of breakdown of the skin (such as though MMP degradation of the dermal matrix and inhibition of procollagen synthesis) concomitant with a decrease in the pathway activity that promotes cell growth (such as a decrease in phosphorylated ERK) both contribute to chronoaging of human skin. Our methods for preventing and rejuvenating chronologically-aged skin, while tested on unexposed, sun-protected skin, often with occlusion of the site treated, are thus applicable to treating chronoaging of the skin over the entire body, including the face and hands.

Taken with the teachings of the aforementioned patent and provisional applications directed to photoaging, daily application of a retinoid to the skin will ameliorate the effects of natural aging as well as the sun's exacerbating effects on natural aging of the skin.

The graphic results of our novel treatments are shown in FIG. 13. FIGS. 13A and 13B are photomicrographs showing the histology appearance of sun-protected skin of a 22-year old individual, the portion in FIG. 13B being an enlarged view of the boxed area in FIG. 13A. As shown therein, the skin is composed of the epidermis E overlying the dermis D. Part of the adhesion between the epidermis and the dermis is facilitated by a larger than apparent interfacial area between the epidermis and the dermis. This interface is defined by the rete pegs or ridges R that extend down from the epidermis into the dermis and by the dermal papillae D that extend up from the dermis into the epidermis. These pegs and papillae create the folds seen in the cross-section of FIG. 13A and increase the interfacial surface area between the two layers of the skin. The section at the bottom (FIG. 13B) shows a more detailed view of the dermis which contains few cells C and is mostly collagen L. As seen in this section from a younger individual, the collagen in the dermis is relatively dense and of a uniform structure.

FIGS. 13C and 13D show the histology of vehicle-treated sun-protected skin of an 86-year old individual. As seen in FIG. 13C from aged skin, the epidermis is thinner in aged skin and there are essentially no rete pegs and essentially no dermal papillae. The detailed view in FIG. 13D shows that dermis of aged skin generally has fewer cells and collagen that is less dense and more unevenly distributed than that found in younger individuals. The thinner epidermis and decreased interfacial surface area between the epidermis and dermis tends to cause elderly people to have a higher incidence of bruising and ulcerous conditions, such as Bateman's purpura.

FIGS. 13E and 13F depict retinol-treated, sun-protected skin from the same individual from whom the biopsy in FIGS. 13C and 13D were taken, after 7 days having been treated as just described (one application of retinol). The changes to the skin shown are quite remarkable and unexpected. The epidermis has thickened, the interfacial surface area has increased due to the presence of new rete pegs and dermal papillae, and as shown in the detailed view, the dermal collagen has become denser and more regular in its appearance. Thus, the topical application of an effective amount of a retinoid acts to normalize the thickness of the epidermis (i.e., normalize with respect to young skin), promote the formation of rete pegs and dermal papillae, and increase the amount, density, and regularity of the collagen in the dermis. These changes reverse the apparent histological changes seen in aged skin and help to prevent bruising, tearing, ulceration, and similar trauma in aged skin that does not occur in young skin.

Graphic results are also shown in FIGS. 18A, 18B, and 18C, stained photomicroph cross-sections, where retinol treatment decreases c-Jun levels (18A) and increases both type I procollagen levels (18B) and type III procollagen levels (18B) after treatment of elderly skin with retinol.

The compositions described herein formulated on a commercial basis can include various conventional colorants, fragrances, thickeners (such as xanthan gum), preservatives, humectants, emollients, demulcents, surfactants, dispersants, penetration enhancers, and the like can be added to provide additional benefits and improve the feel and/or appearance of the topical preparation. Likewise, the composition can be formulated as a cream, lotion, ointment, soap or body wash, shampoo, or a mask.

The foregoing description and following methods are meant to be illustrative of the invention and not limiting. Various changes, modifications, and additions may become apparent to the skilled artisan upon a perusal of this specification, and such are meant to be within the scope and spirit of the invention as defined by the claims.

Methods Used in the Examples

Histology and morphometry. Replicate 4-mm punch biopsies were obtained from buttock skin of each individual. Formalin-fixed tissue pieces were sectioned, stained with hematoxylin and eosin, randomized and blinded. The sections were examined using an Olympus BX40 microscope in conjunction with a Sony DCX-151 high-resolution camera. Blocked areas 200 $\mu$m on a side were isolated using NIH Imager software and epidermal height was assessed at four sites (25 $\mu$m apart) in each of two such areas. The same two blocked areas were used for epithelial cell counts. The number of interstitial cell nuclei (i.e., nuclei below the dermo-epidermal juncture, not associated with capillaries) over the entire histological section was determined as a measure of dermal cellularity. The same blinded sections were scored for connective tissue fiber spacing, thickness, degree of disorganization and depth of disorganization, using a scale of 1–9 for each parameter.

Ex vivo cell growth. Biopsies were minced into small fragments approximately 15 fragments per tissue piece)and the tissue fragments transferred to plastic cell culture flasks. Culture medium consisted of Dulbecco's Modified Minimal Essential Medium of Eagle with Earle's salts, non-essential amino acids and 10% fetal bovine serum. Tissue fragments were incubated at 37° C. and 5% $CO_2$/95% air for up to one month. Each fragment was scored for whether keratinocytes and/or fibroblasts grew out of the tissue and from this, the percentage of fragments from which keratinocytes and fibroblasts were isolated was determined according to the method of Varani, J., et al., *J. Clin. Invest.*, 96, 1747–1756 (1994).

Matrix metalloproteinase assays. Tissue pieces were frozen in liquid nitrogen immediately after biopsy, homogenized in 20 mM Tris HCl (pH 7.6) plus 5 mM $CaCl_2$, and centrifuged at 3000×g for 10 minutes to remove particulates. Ability to release soluble radioactive fragments from 3H-labeled fibrillar type I collagen (described by Fisher, G. J., et al., *Nature*, 379, 335–339 (1996) and Hu, C-L, et al., *Analytic. Biochem*, 88, 638–643 (1978)) was used as a measure of collagenolytic activity. Tissue extracts were incubated for 3 hours with 1 mM aminophenyl mercuric acetate (APMA) to convert the inactive form of the matrix metalloproteinase into an active form. Subsequently, 0.2 $\mu$Ci of collagen substrate (NEN-DuPont, Boston, Mass.) was incubated for 24 hours with 50 $\mu$l of tissue extract. At the end of the 24-hour incubation period, the samples were centrifuged at 12,000×g for 10 minutes to pellet the intact protein. Radioactivity remaining in the supernatant fluid was then measured and from this, the percentage of substrate hydrolzyed was determined.

Gelatin zymography (Varani et al., op. cit.) was used to assess MMP-2 (72-kD gelatinase; gelatinase A) and MMP9 (92-kD gelatinase; gelatinase B) activity. Tissue extracts were electrophoresed in an 8.5% SDS-polyacrylamide gel containing 1 mg/ml of gelatin. After electrophoresis, the SDS was removed by three sequential washes in 1% Triton X-100. The first two washes were for 20 minutes each and the last was overnight. Quantitation of hydrolysis zone width was done by laser densitometry.

What is claimed is:

1. A method for delaying the decrease in collagen inherent in naturally-aged (chronologically-aged) human skin, comprising: providing a composition including a non-toxic amount of retinoid in a cosmetically suitable vehicle and applying said composition to the skin on a regular basis in an amount effective to delay both the decrease in procollagen biosynthesis and the increase in enzymatic collagen degradation inherent in naturally-aged human skin.

2. The method of claim 1, wherein the skin is sun-protected skin.

3. The method of claim 1, wherein the retinoid is selected from retinol, retinal, retinoic acid, a retinoic acid salt, a derivative or analog thereof, or a mixture thereof.

4. The method of claim 3, wherein the retinoid is retinol or a mixture of retinol and retinoic acid.

5. The method of claim 1, wherein the retinoid is applied daily.

6. The method of claim 1, further comprising the topical administration of an effective, non-toxic amount of a non-retinoid MMP inhibitor.

7. The method of claim 6, wherein the MMP inhibitor is selected from aspirin, E5510, glucocorticoids, Vitamin $D_3$, GI12947, TIMPs, hydroxamates and hydroxy-urea derivatives, and tetracyclines and derivatives thereof, and the various salts thereof, and compatible mixtures thereof.

8. The method of claim 6, wherein the MMP inhibitor is selected from the group consisting of genistein, galardin, batimastat, marimastat, N-acetyl cysteine, and green tea extract.

9. The method of claim 6, wherein said retinoid and said MMP inhibitor are present in a single, topically administered formulation.

10. The method of claim 7, wherein said retinoid and said MMP inhibitor are present in a single, topically administered formulation.

11. The method of claim 8, wherein said retinoid and said MMP inhibitor are present in a single, topically administered formulation.

12. A method for delaying the increase in collagen degradation inherent in naturally-aged (chronologically-aged) human skin, comprising, providing a composition including a non-toxic amount of non-retinoid MMP inhibitor in a cosmetically-suitable vehicle and applying said composition to the skin on a regular basis in an amount effective to delay the increase in enzymatic collagen degradation inherent in naturally-aged human skin.

13. The method of claim 12, wherein the MMP inhibitor is selected from aspirin, E5510, glucocorticoids, Vitamin $D_3$, GI12947, TIMPs, hydroxamates and hydroxy-urea derivatives, and tetracyclines and derivatives thereof, and the various salts thereof, and compatible mixtures thereof.

14. The method of claim 12, wherein the MMP inhibitor is selected from the group consisting of genistein, galardin, batimastat, marimastat, N-acetyl cysteine, and green tea extract.

15. The method of claim 12, further comprising the topical application, on a regular basis, of a retinoid.

16. The method of claim 15, wherein the topical application of the retinoid and the MMP inhibitor are concurrent.

17. The method of claim 15, wherein the topical application of the retinoid and the MMP inhibitor are not concurrent.

18. The method of claim 15, wherein the retinoid is retinoic acid, retinol, or a mixture thereof.

* * * * *